United States Patent
Dauson et al.

(10) Patent No.: US 10,155,222 B2
(45) Date of Patent: Dec. 18, 2018

(54) DEVICE FOR THE SEPARATION OF PARTICLES USING A BULK ACOUSTIC WAVE FIELD

(71) Applicant: CARNEGIE MELLON UNIVERSITY, a Pennsylvania Non-Profit Corporation, Pittsburgh, PA (US)

(72) Inventors: Erin R. Dauson, Pittsburgh, PA (US); David W. Greve, Pittsburgh, PA (US); Irving J. Oppenheim, Pittsburgh, PA (US); Kelvin B. Gregory, Pittsburgh, PA (US); Gregory P. Healy, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 71 days.

(21) Appl. No.: 15/269,836

(22) Filed: Sep. 19, 2016

(65) Prior Publication Data
US 2017/0080423 A1 Mar. 23, 2017

Related U.S. Application Data

(60) Provisional application No. 62/283,999, filed on Sep. 17, 2015, provisional application No. 62/390,207, filed on Mar. 22, 2016.

(51) Int. Cl.
*B01L 3/00* (2006.01)
*G01N 15/10* (2006.01)
(Continued)

(52) U.S. Cl.
CPC ..... *B01L 3/502761* (2013.01); *B01L 3/50273* (2013.01); *B01L 3/502707* (2013.01);
(Continued)

(58) Field of Classification Search
CPC ......... B01L 3/502761; B01L 3/502707; B01L 3/502715; B01L 3/50273; B01L 3/502776;
(Continued)

(56) References Cited

U.S. PATENT DOCUMENTS 5,006,266 A * 4/1991 Schram ............... B01D 21/283
209/1
6,082,180 A * 7/2000 Greenwood ............ G01N 9/24
73/32 A
(Continued)

OTHER PUBLICATIONS

Dauson, Erin. "Microparticle separation using bulk acoustic waves in a PMMA prism with a tilted-angle channel." Doctoral Dissertation, Carnegie Mellon University, Pittsburgh, PA (2015).
(Continued)

*Primary Examiner* — Natalie Huls
*Assistant Examiner* — Monica S Young
(74) *Attorney, Agent, or Firm* — Michael G. Monyok; David G. Oberdick (57) ABSTRACT

The disclosure describes a prism containing a microfluidic channel. By coupling bulk acoustic wave generators to opposing sides of the prism, a standing bulk acoustic wave field can be excited in the prism and in the microfluidic channel. Because the microfluidic channel is titled with respect to the nodes of the bulk acoustic wave field, the prism microfluidic channel device can be used to separate microparticles and biological cells by size, compressibility, density, shape, or mass distribution. This technology enables high throughput cell sorting for biotechnology applications such as cancer cell detection.

9 Claims, 6 Drawing Sheets

(51) Int. Cl.
*G01N 1/40* (2006.01)
*G01N 15/02* (2006.01)
*G01N 15/00* (2006.01)

(52) U.S. Cl.
CPC ... *B01L 3/502715* (2013.01); *B01L 3/502776* (2013.01); *G01N 1/4077* (2013.01); *G01N 15/0255* (2013.01); *G01N 15/1056* (2013.01); *B01L 2200/025* (2013.01); *B01L 2200/0652* (2013.01); *B01L 2200/12* (2013.01); *B01L 2300/0867* (2013.01); *B01L 2300/12* (2013.01); *B01L 2400/0436* (2013.01); *G01N 2015/0019* (2013.01); *G01N 2015/0065* (2013.01); *G01N 2015/1081* (2013.01)

(58) Field of Classification Search
CPC ....... B01L 2200/025; B01L 2200/0652; B01L 2200/12; B01L 2300/0867; B01L 2300/12; B01L 2400/0436; G01N 1/4077; G01N 15/0255; G01N 15/1056; G01N 2015/0065
USPC ....................................................... 73/570.5
See application file for complete search history.

(56) References Cited

U.S. PATENT DOCUMENTS

2009/0147253 A1* 6/2009 Hartmann ......... B01L 3/502715
356/246
2014/0033808 A1* 2/2014 Ding ...................... G01N 29/02
73/61.75

OTHER PUBLICATIONS

Shi, Jinjie et al. "Continuous particle separation in a microfluidic channel via standing surface acoustic waves (SSAW)." Lab on a Chip 9, No. 23 (2009): 3354-3359.

Johansson, Linda et al. "Surface acoustic wave induced particle manipulation in a PDMS channel—principle concepts for continuous flow applications." Biomedical microdevices 14, No. 2 (2012): 279-289.

Bernate, Jorge A. et al. "Vector separation of particles and cells using an array of slanted open cavities." Lab on a Chip 13, No. 6 (2013): 1086-1092.

Altuglas International, Arkema Group. "Plexiglas® General Information and Physical Properties." Aug. 2006. <http://www.plexiglas.com/export/sites/plexiglas/.content/medias/downloads/sheet-docs/plexiglas-general-information-and-physicalproperties.pdf>.

Dauson, Erin R. et al. "Surface acoustic wave action on microfluidic channels and microparticles." In SPIE Smart Structures and Materials+ Nondestructive Evaluation and Health Monitoring, pp. 906102-906102. International Society for Optics and Photonics, 2014.

Oppenheim, Irving J. et al., "Microparticle transport and concentration with surface acoustic waves." In SPIE Smart Structures and Materials+ Nondestructive Evaluation and Health Monitoring, pp. 86921D-86921D. International Society for Optics and Photonics, 2013.

Dauson, Erin R. et al., "Mechanically robust microfluidics and bulk wave acoustics to sort microparticles." In SPIE Smart Structures and Materials+ Nondestructive Evaluation and Health Monitoring, pp. 98051I-98051I. International Society for Optics and Photonics, 2016.

Dauson, E. R. et al., "Particle separation using bulk acoustic waves in a tilted angle microfluidic channel." In Ultrasonics Symposium (IUS), 2015 IEEE International, pp. 1-4. IEEE, 2015.

Chen, Y., et al., "Continuous enrichment of low-abundance cell samples using standing surface acoustic waves (SSAW)," Lab Chip, vol. 14, No. 5, pp. 924-930, 2014.

Ding, X. et al., "Cell separation using tilted-angle standing surface acoustic waves," Proc. Natl. Acad. Sci., vol. 111, pp. 12992-12997, 2014.

Li, P., et al., "Acoustic separation of circulating tumor cells," Proc. Natl. Acad. Sci. U. S. A., vol. 112, No. 16, pp. 4970-4975, 2015.

Li, S. et al., "Standing surface acoustic wave (SSAW)-based cell washing," Lab Chip, vol. 15, No. 1, pp. 331-338, 2015.

Frank, A., et al., Separation of Suspended Particles by use of the Inclined Resonator Concept, Ultrasonics International 93, pp. 519-522, Elsevier, 1993.

Evander, M., et al., "Microfluidic PMMA interfaces for rectangular glass capillaries," J. Micromechanics Microengineering, vol. 24, No. 2, p. 027003, 2014.

* cited by examiner

DEVICE FOR THE SEPARATION OF PARTICLES USING A BULK ACOUSTIC WAVE FIELD

CROSS-REFERENCE TO RELATED APPLICATIONS

This application claims the benefit under 35 U.S.C. § 119 of Provisional Application Ser. No. 62/283,999, filed Sep. 17, 2015, and Provisional Application Ser. No. 62/390,207, filed Mar. 22, 2016, each of which is incorporated herein by reference.

STATEMENT REGARDING FEDERALLY SPONSORED RESEARCH

This invention was made with government support under Grant No. CMMI-1235145 awarded by the U.S. National Science Foundation. The government has certain rights in the invention.

BACKGROUND OF THE INVENTION

This invention relates generally to the separation of particles. More specifically, the invention relates to the separation of particles suspended in a fluid through the use of acoustic forces.

Separating and sorting particles is an important activity in many applications including biological research, cellular engineering, biological and chemical analyses, and lab-on-a-chip technologies. Several methods exist for particle separation, but each has its own drawbacks. For example, magnetic, electrokinetic, and dielectrophoretic separation methods rely on the particles having an inherent charge, polarization, or magnetization. When the particles are biological cells, modifying the cells to obtain these properties can adversely impact the cell physiology and viability, rendering the techniques unusable for cellular engineering applications. Hydrodynamic separation mechanisms, including flow cytometry, can be continuous and passive, but these techniques are limited in volumetric flow rate or require contact between the particle and channel structure.

Alternatively, using acoustic forces in microfluidic particle and cell separation devices provides a promising solution to the limitations of many other methods. Acoustic particle separation is label-free and can separate particles based on physiological properties including shape, density, size, and compressibility. The use of the acoustic force is contactless and does not require any specific particle property, labeling, or tagging. Moreover, the acoustic force on biological cells does not appear to have a significant deleterious effect on the particle viability, making acoustic microfluidics an ideal method for cell separation, especially when downstream processing and analyses requires the cell physiology to remain unmodified.

According to one known acoustic method, particles are separated using standing surface acoustic waves (SAW). These types of devices, which are typically molded with soft polymers (such as in a polydimethylsiloxane), are not robust enough for use outside of a lab and are expensive to fabricate. Further, the flowrate of fluid in the device is limited because the useful standing waves are confined to a distance from the bottom surface of the channel, typically resulting in a shallow channel. It would therefore be advantageous to develop an improved device for sorting particles using acoustic forces, and a method of manufacturing the same, that are more robust and offer greater throughput.

BRIEF SUMMARY

According to one embodiment of the present invention is a device employing standing bulk acoustic waves to separate particles flowing in a channel, where the nodes of the standing waves are at an angle to the direction of flow of a fluid through the channel. Within the microfluidic channel, the particles experience an acoustic force towards the acoustic nodes, which is proportional to the particle volume. The acoustic force is opposed by the drag force on the particle from the fluid, which is proportional to particle radius. Consequently, particles with a larger volume move faster towards acoustic nodes than smaller volume particles. By applying the acoustic forces at an angle to the direction of flow, it is possible to separate particles by size or other characteristic in a continuous flow device.

In one embodiment, the device comprises a prism containing a microfluidic channel and bulk acoustic wave transducers positioned on opposing sides of the prism. Using the transducers, bulk acoustic wave energy can be excited through the prism to create acoustic pressure fields in the microfluidic channel. Specifically, nodes (and antinodes) form in parallel lines within the fluid passing through the microfluidic channel. Notable, the standing wave is present throughout the depth of the channel and is not limited to a surface of the channel. In one embodiment, the node line spacing is on the order of 100 μm for particles of interest in the range of 1-20 μm.

The present invention can be used to separate many different types of microparticles, such as bacteria or cells. One example application includes cancer cell detection in blood. Particle separation using the acoustic force can be done with live cells or bacteria and is not destructive so it can be integrated into other lab-on-a-chip type devices to examine particles after separation.

DETAILED DESCRIPTION

Figure 2:
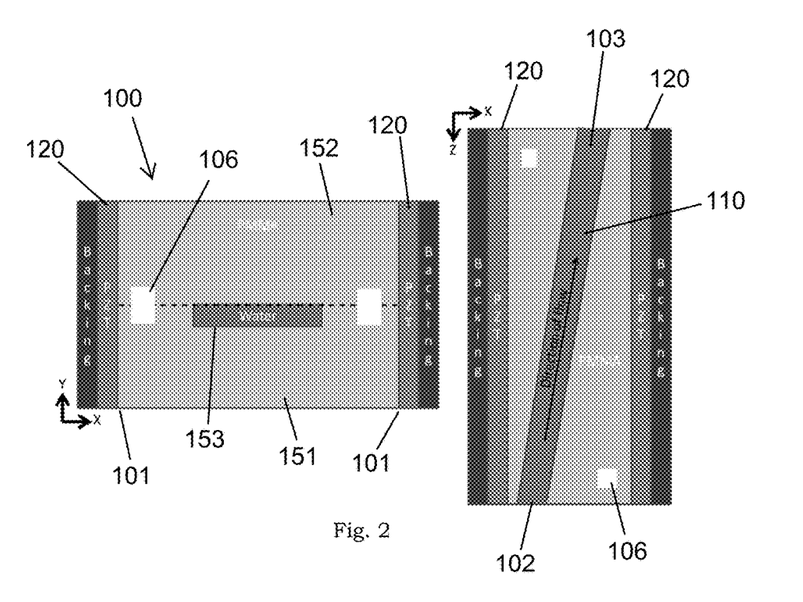
FIG. 2 is cross section views of the particle separation device according to one embodiment.
Figure 3:
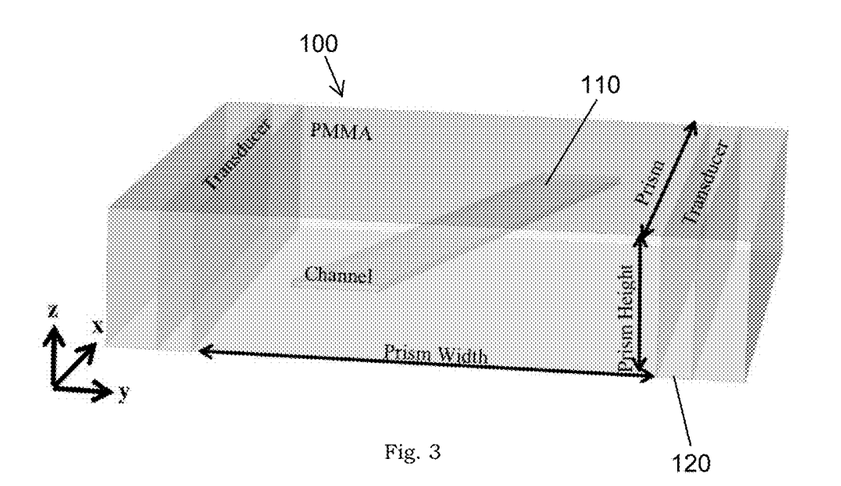
FIG. 3 is an alternative view of the particle separation device.

According to one embodiment, the separation device comprises a prism 100, a microfluidic channel 110 within the prism 100, and a pair of bulk acoustic wave generators 120 attached to the prism. As shown in FIG. 2, the prism 100 is generally rectangular in shape and is constructed from poly (methyl methacrylate) (PMMA) in one embodiment, although other rigid polymers or materials can be used. The acoustic wave generators 120 are coupled to opposing external sides 101 of the prism 100 and are used to create standing or traveling waves within the microchannel 110. However, separation along node lines is more effective in standing wave environments. To create standing waves, the acoustic wave generators 120 are positioned parallel to each other on opposing sides of the channel 110. In one embodiment, the acoustic wave generators 120 are lead zirconate titanate (PZT) transducers; however, other types of bulk acoustic wave generators can be used. FIGS. 2-3 depict alternative embodiments of the separation device.

Figure 1:
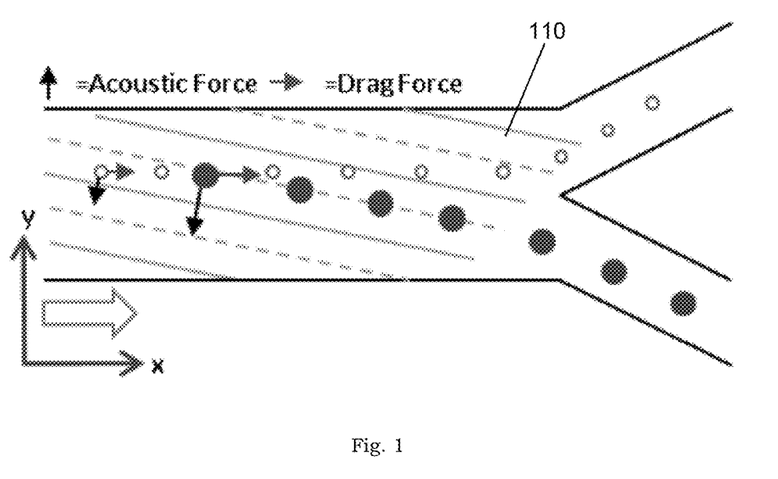
FIG. 1 is a diagram illustrating the effect of drag and acoustic forces on different particles.

The channel 110 is fabricated at an angle with respect to the transducers 120. This configuration is identified as the "tilted angle" geometry. Because the standing waves are substantially parallel to the transducers 120, the standing waves are angled to the direction of flow in the channel 110. In one embodiment, the angle of the channel 110 relative to the standing waves is between 10 and 45 degrees. However, as will be discussed, the angle of the channel 110 can vary depending on the particles to be separated and other design parameters. FIG. 1 is an illustration of the titled angle geometry where the node lines are shown at an angle to the direction of flow.

Applying the acoustic force at an angle with respect to the flow is advantageous because the separation distances are limited only by the size of the channel 110. In contrast, when parallel configurations are used the separation distance is limited to a fraction of the acoustic wavelength. The title angle geometry enables a device with higher throughput and separation of particles closer in size.

Figure 8:
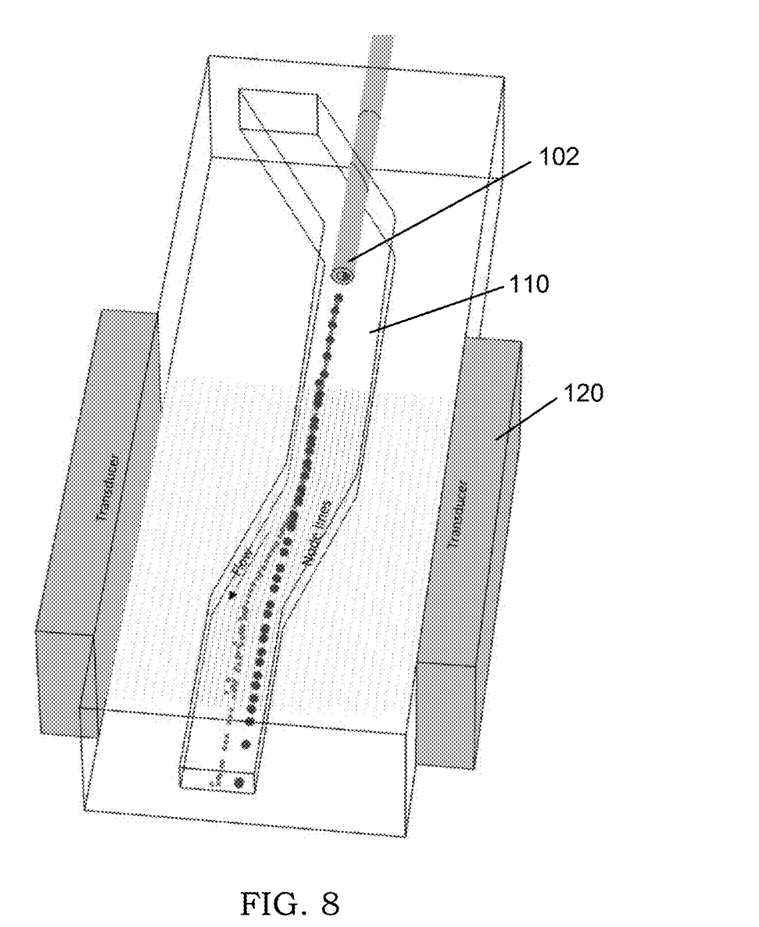
FIG. 8 shows the separation device having a coaxial inlet, according to one embodiment.

To introduce the fluid to the prism and collect the effluent, inlet 102 and outlet 103 are provided on the prism 100. The inlet 102 provides an entry point for the particles into the microchannel 110. The particles are suspended in a fluid such as water, traveling through the channel 110 in a laminar or streamline flow. In one embodiment, the inlet 102 and outlet 103 are coplanar with the channel 110. FIG. 8 shows an inlet 102 that is coaxial with the microchannel 110.

Figure 6:
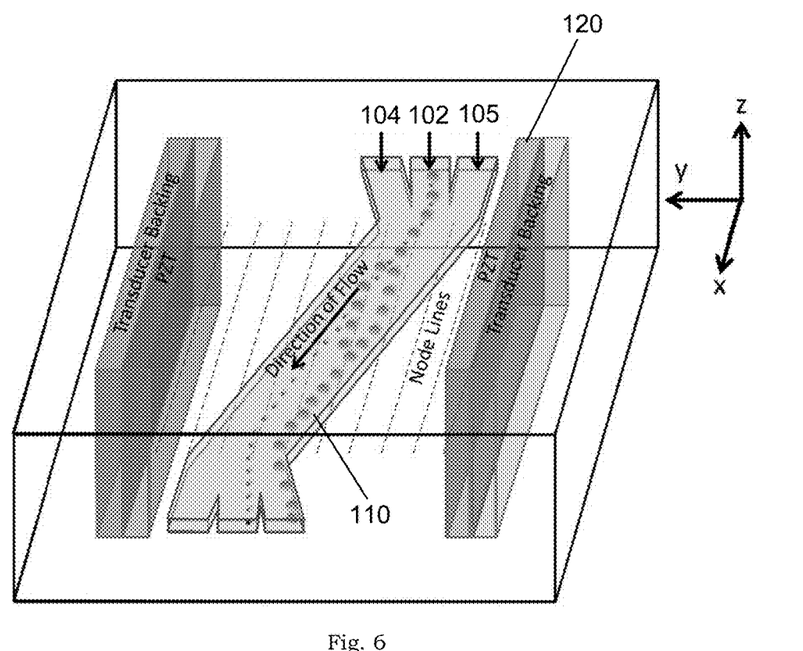
FIG. 6 is an illustration of another example embodiment.

In an alternative embodiment, additional inlets 104 and 105 are provided for sheath flow, as seen in FIG. 6, around the inlet flow. More specifically, the additional inlets 104 and 105 provide a flow of fluid that does not contain particles around the particle stream, concentrating the particles to the center of the channel 110. In the embodiment with sheath flow, the particles are concentrated at the center of the channel 110 before separation begins by controlling the ratio of the suspended particle volumetric flow rate to the sheath fluid volumetric flow rate. Without sheath flow, the particles start distributed across the channel 110 and the separation will be incomplete since some small particles are positioned at the part of the channel where the larger particles are ending. In addition to focusing particles within the width of the cannel 110, the particles can be focused towards the mid-height of the channel 110 by making the inlet 103 shallower than the additional inlets 104 and 105. This is particularly advantageous in bulk acoustic devices since the acoustic wave is present through the depth of the channel 110.

For example, in one embodiment, the node lines in the channel are oriented vertically along the height of the channel and spaced evenly along the width of the channel. The channel must be wide enough to include multiple node lines (more node lines can allow for greater separation), but narrow enough for both acoustic uniformity and a sufficient flow velocity (given the volumetric flow rate) for separation.

When the channel is tilted with respect to the transducers 120 (and thus tilted to the node lines of the standing waves), the drag and acoustic forces have components transverse to the channel. Because of the difference in the relationship between the acoustic force and the drag force on particles of different sizes in the same acoustic field, larger particles more closely follow the node lines of the acoustic field, taking an undulating path from node line to node line. Conversely, the smaller particles more closely follow the streamlines of the flow. Thus, the difference in forces enables particle separation. Acoustic forces can also affect particles differently based on their density, compressibility, shape, and mass distribution. FIG. 1 depicts the differences in magnitude between drag and acoustic forces for two different sized particles.

Figure 4:
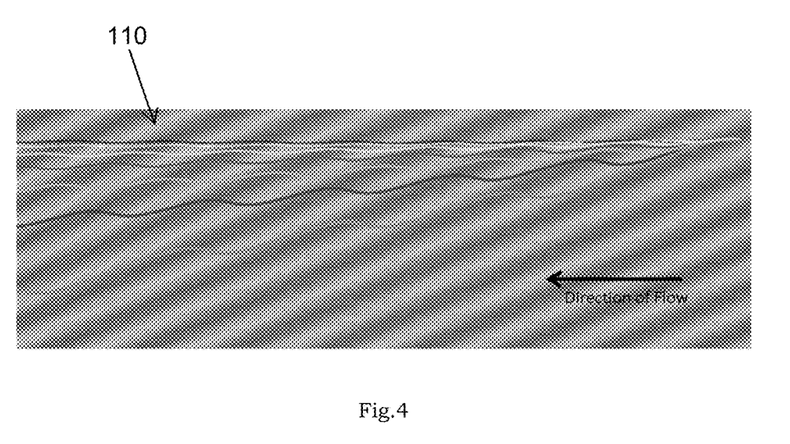
FIG. 4 path lines for particles ranging in size from 3 μm to 9 μm in a tilted angle acoustic field with microfluidic flow.

With the appropriate choice of device and operational parameters, the balance between the acoustic force and the drag force on particles enables separations. However, depending on particle type, flow rate, acoustic energy, and channel size, particles can take different paths within the channel 110. While it is beneficial to have the particles to be separated follow one of two different paths, several different trajectories are possible depending on the parameters of device construction and operation. In the separation device, a particle can follow one of three distinct trajectories: (1) the particle follows the fluid streamline with no "deflection" by acoustic effects; (2) the particle follows an undulating path; (3) the particle follows a path to a node line and remains in the node line. FIG. 4 is an example of paths followed by different particle sizes ranging from 3 µm to 9 µm. Notice the smallest particle follows a fairly straight path, whereas the largest particle undulates from node to node.

Figure 7:
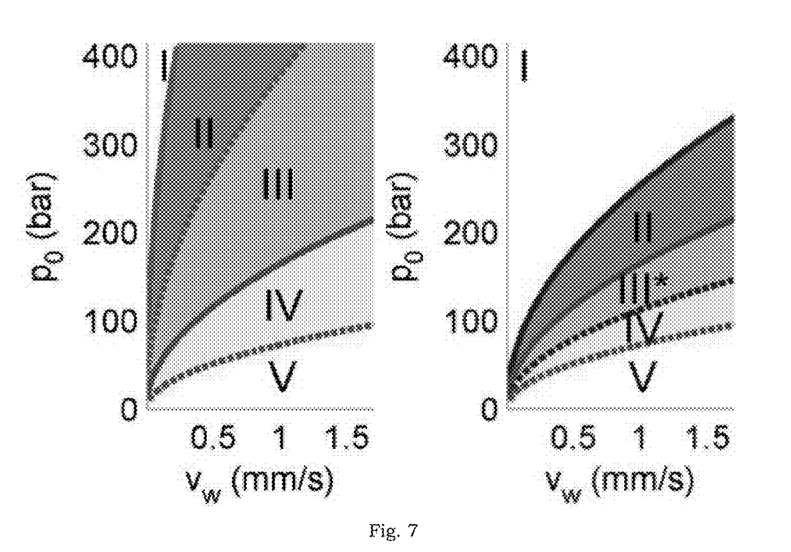
FIG. 7 is a graph depicting various regions defining a particle path.

Plotting acoustic pressure against water velocity, four parabolas are produced that divide the design space into five regions. The plot is shown in FIG. 7. The condition of four distinct regions (labeled I through IV) are described physically as follows.

In region I, the acoustic force on a particle is sufficiently large, relative to the fluid force, that 15 µm and 2 µm particles all deflect to a node line, and separation does not occur.

In region II, 15 µm particles deflect to a node line while 2 µm particles follow an undulating path, because the trajectory of a large particle is more sensitive to acoustic pressure than that of a small particle. Separation is possible, in principle, but is not maximally effective.

In region III, 15 µm particles deflect to a node line while 2 µm particles do not deflect. This achieves maximal, robust separation.

In region IV, 15 µm particles follow an undulating path 2 µm particles do not deflect. Separation is possible, in principle, but not maximally effective.

(Region V, not labeled, is the area on the abscissa of low acoustic pressure in which neither particle deflects.)

Given that PMMA prisms 101 are rapidly prototyped, different sizes can be created if the velocity and pressure parameters cannot be varied sufficiently to achieve the desired separation.

To fabricate the prism 100, micromachining technology is utilized. For example, the microfluidic channel 110 can be milled at a sub-mm scale on a Mini-Mill desktop CNC system from Minitech Machinery Corp. In alternative embodiment, the each part of the prism is printed using additive manufacturing techniques (or 3D printing). However the device can also be fabricated using embossing or casting techniques.

In one example fabrication method using micromachining, the prism 100 is formed from two half-pieces (a first part 151 and a second part 152) joined together. In this example, the first part 151 and the second part 152 are manufactured from PMMA stock 3.175-mm thick. As shown in FIG. 2, the first part 151 is milled is milled with a 0.05 inch end mill to create a groove 153 300 microns deep on its surface. The second part 152 has a flat surface. Both half-pieces 151,152 are milled to form inlet/outlet segments, alignment mechanism 106, and transducer through-slots. The alignment mechanism 106 (shown in FIG. 2), such as an alignment key, allow 'snap-together' assembly with sufficient precision to create complex channels 110 and to present a planar face on the exterior of the prism 100 for uniform acoustic coupling. For example, the transducers 120 are contained within slots and coupled acoustically to the prism 100 with water, way oil, or acoustic coupling gel. To complete assembly, the two half-pieces 151, 152 are bonded by cleaning first with soap and water, ashing the faces to be bonded in a Harrick Plasma Cleaner (in air) for five minutes, and then clamping the two pieces between glass plates and baking in an oven at 305 degrees F. for 60 minutes. This fabrication technique allows for very rapid prototyping of different designs.

Given the relative ease of micromachining a custom channel 120 profile, in one embodiment the method of fabricating a device further comprises simulating the separation dynamics to determine the optimal device configuration. For example, according to one embodiment, COMSOL 4.3b Multiphysics Software is used to model particle motion in a channel 1270 µm wide and 150 µm deep tilted 20° with respect to the acoustic field. However, any simulation software can be used. The fluidic medium is water with a velocity of 10 mm/s. Using the particle tracing with mass postanalysis function in COMSOL, 3 µm to 9 µm diameter particles are simulated including the drag force from the fluid and the force due to the acoustic field. An analytic expression was used for the acoustic force given by:

$$F_{\hat{x}} = -\left(\frac{4\pi^2 p_0^2 r^3 \beta_m}{6\lambda}\right)\left(\frac{5\rho_p - 2\rho_m}{2\rho_p + \rho_m} - \frac{\beta_p}{\beta_m}\right)\sin\left(\frac{4\pi}{\lambda}(\hat{x}\sin(\theta) - \hat{y}\cos(\theta))\right)\sin(\theta) + 6\pi\eta r(v_w - \dot{\hat{x}}) \text{ and}$$

$$F_{\hat{y}} = -\left(\frac{4\pi^2 p_0^2 r^3 \beta_m}{6\lambda}\right)\left(\frac{5\rho_p - 2\rho_m}{2\rho_p + \rho_m} - \frac{\beta_p}{\beta_m}\right)\sin\left(\frac{4\pi}{\lambda}(\hat{x}\sin(\theta) - \hat{y}\cos(\theta))\right)\cos(\theta) + 6\pi\eta r\dot{\hat{y}}$$

where $\hat{x}$ is the particle coordinate along the channel, $\hat{y}$ is the particle coordinate across the channel, $p_0$ is the acoustic pressure which controls the amplitude of the force, r is the particle radius, $\rho$ is the density of the particles and the medium, water, p and m respectively, $\beta$ is the compressibility of the particles and the medium, $\lambda$ is the wavelength, 200 µm, and $\theta$ is the tilt angle of the channel.

This equation represents the force from the acoustic field created by acoustic waves incident from both sides of the channel. Using this simulation, parameters can be varied to achieve separation for a given particle size.

Figure 5:
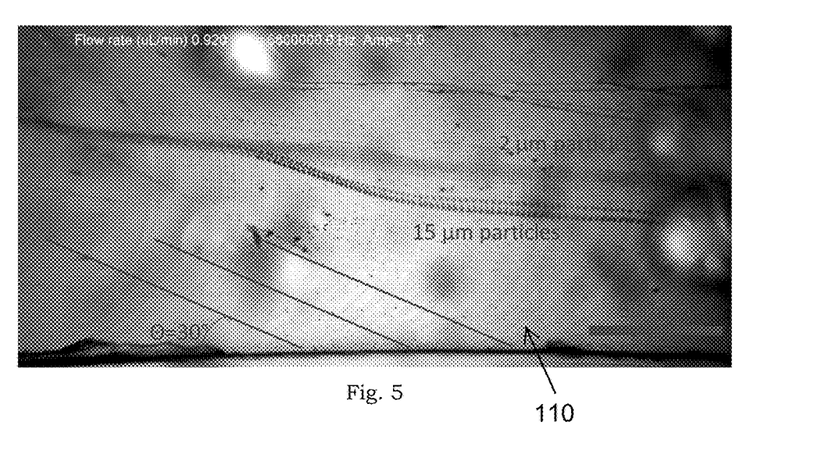
FIG. 5 is an image showing the path of two different sized particles in a separation device according to one embodiment.

Because bulk acoustic waves enter the microfluidic channel from the sides (unlike a SAW device where the waves enter from the bottom), the nodal separation is dependent only on the acoustic frequency and acoustic velocity in the fluid. Thus, node lines with 100 micron spacing require a frequency of about 7.41 MHz. In one example device, separation of 2 µm and 15 µm polymer spheres suspended in water was accomplished by driving the transducers 120 with 33V amplitude at 6.8 MHz, which is a resonant frequency of some PZT transducers 120, and gives a node spacing of about 113 microns. This example is shown in FIG. 5.

In one example embodiment, the channel has a width of 1.27 mm, a height of 300 µm, a length of about 4-5 mm, and a tilt angle of 15° or 30° with respect to the exterior walls 101 of the prism 100. In this particular embodiment, the prism 100 has a height of 5.08 mm and a width of 4.34 mm. However, a wide range of dimensions, shapes, and other design parameters may work.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A particle separation device comprising:
   a prism comprising a first side and a second side parallel to the first side;
   a microchannel formed in an interior portion of the prism, wherein a longitudinal axis of the microchannel is not parallel to the first side and the second side;
   a first bulk acoustic wave generator acoustically coupled to the first side of the prism;
   a second bulk acoustic wave generator acoustically coupled to the second side of the prism,
   wherein the first bulk acoustic wave generator and he second bulk acoustic wave generator transmit wave energy through the prisom to create an acoustic pressure field in the microchannel, thereby forming at least one standing wave within the microchannel, wherein a node line of the at least one standing wave is not parallel to a side of the microchannel.

2. The separation device of claim 1, wherein the prism comprises poly (methyl methacrylate).

3. The separation device of claim 1, wherein the prism comprises a rigid polymer.

4. The separation of device of claim 1, wherein the prism comprises:
   a first part having a groove disposed on the surface of the first part;
   a second part substantially matching the shape of the first part and having a surface,
   wherein the surface of the first part is mated to the surface of the second part forming the microchannel.

5. The separation device of claim 4, further comprising:
   an alignment mechanism on the surface of the first part;
   a complementary alignment mechanism on the surface of the second part, wherein the alignment mechanism of the first part engages the complementary alignment mechanism of the second part when the first part is mated to the second part to align the first part with the second part.

6. The separation device of claim 5, wherein the alignment mechanism of the first part is a pin and the complementary alignment mechanism of the second part is a hole.

7. The separation device of claim 1, wherein the first acoustic wave generator and the second acoustic wave generator comprise lead zirconate titanate.

8. The separation device of claim 1, further comprising:
   an inlet in communication with the microchannel, wherein the inlet and the microchannel are coaxial.

9. The separation device of claim 8, further comprising:
two additional inlets positioned on each side of the inlet to provide a sheath flow around a fluid entering the microchannel from the inlet.

* * * * *